United States Patent
DiMaggio

(10) Patent No.: US 6,926,239 B1
(45) Date of Patent: Aug. 9, 2005

(54) MOUNTING ASSEMBLY FOR A WASTE DISCHARGE LINE OF A MEDICAL TREATMENT APPARATUS

(76) Inventor: Edward J. DiMaggio, 45110 Sub Station Rd., Hammond, LA (US) 70401

( * ) Notice: Subject to any disclaimer, the term of this patent is extended or adjusted under 35 U.S.C. 154(b) by 0 days.

(21) Appl. No.: 10/764,230

(22) Filed: Jan. 23, 2004

(51) Int. Cl.[7] ............................................. F16B 47/00
(52) U.S. Cl. .............................. 248/206.1; 248/206.2; 248/302
(58) Field of Search ......................... 248/206.1, 205.1, 248/206.2, 362, 302, 339, 205.5, 205.6, 205.7, 248/206.3

(56) References Cited

U.S. PATENT DOCUMENTS

| | | | |
|---|---|---|---|
| 1,331,427 A | * | 2/1920 | Frank .......................... 248/27.5 |
| 3,685,680 A | | 8/1972 | Tenckhoff et al. |
| 5,028,026 A | * | 7/1991 | Philipps et al. ........... 248/206.2 |
| 5,148,769 A | * | 9/1992 | Zelinger ...................... 119/708 |
| 5,492,739 A | * | 2/1996 | Thorne et al. ................. 428/38 |
| 5,595,364 A | * | 1/1997 | Protz, Jr. .................. 248/205.5 |
| 6,234,992 B1 | | 5/2001 | Haight et al. |
| 6,237,654 B1 | | 5/2001 | Sheyer |
| 6,280,634 B1 | | 8/2001 | Shah et al. |
| 6,348,162 B1 | | 2/2002 | Ash |
| 6,588,803 B2 | | 7/2003 | Vila |
| 6,632,189 B1 | | 10/2003 | Fallen et al. |
| 6,669,033 B1 | * | 12/2003 | Lian .......................... 211/87.01 |
| 2001/0040202 A1 | * | 11/2001 | Adams .................... 248/206.2 |
| 2002/0023879 A1 | | 2/2002 | Hadden |
| 2002/0077608 A1 | | 6/2002 | Stringer et al. |
| 2002/0123715 A1 | | 9/2002 | Sorenson et al. |
| 2002/0174483 A1 | | 11/2002 | Gallant |
| 2003/0043688 A1 | | 3/2003 | Peterson et al. |
| 2003/0163078 A1 | | 8/2003 | Fallen et al. |
| 2003/0201369 A1 | * | 10/2003 | Dretzka ................... 248/206.2 |

* cited by examiner

Primary Examiner—Ramon O Ramirez
(74) Attorney, Agent, or Firm—Keaty Professional Law Corporation

(57) ABSTRACT

A mounting assembly for a discharge conduit of a medical treatment device, such as a dialysis machine. The mounting assembly has a connector member detachably engageable with a discharge nozzle of a discharge conduit and a suction cup that can be mounted on a rim of a waste receptor, such as a sink or a toilet bow. The mounting assembly supports the discharge nozzle directly above the opening of the waste receptor, thereby facilitating discharge of the liquid waste directly into a municipal sewage line.

5 Claims, 2 Drawing Sheets

MOUNTING ASSEMBLY FOR A WASTE DISCHARGE LINE OF A MEDICAL TREATMENT APPARATUS

BACKGROUND OF THE INVENTION

This invention relates to an accessory for a medical treatment apparatus, such as for instance, a dialysis machine, and more particularly to a support assembly for a drainage tube that is used to promote the drainage of fluids from a waste side of a dialysis machine in an efficient and sanitary manner.

The kidneys perform one of the most important functions in the elimination of waste in a human body; they filter out extra water and waste, thereby cleaning the blood and facilitating production of an adequate level of red blood cells. When the kidneys fail, the fluids are retained in the blood and do not circulate in the proper fashion through the body. As a consequence, waste material builds up in the body seriously endangering health and wellbeing of the person.

Dialysis imitates the work of a kidney. Technology has developed two types of dialysis treatment: hemodialysis and peritoneal dialysis. The majority of the patients receive hemodialysis, by which the blood is circulated outside the body and cleaned inside the machine before returning to the patient. The patent's blood is drained into the dialysis machine and a fluid called dialysate is also circulated through the machine. A thin, semi-permeable membrane separates the part that circulates the blood and the second part for the dialysate. As dialysate processes on one side of the membrane, and blood on the other, particles in waste from the blood stream pass through the microscopic holes formed in the membrane and are washed away in the dialysate. Blood cells being too large to go through the membrane holes are returned to the body.

The other type of treatment, peritoneal dialysis, uses the patient's own peritoneal membrane as a filter. The peritoneal membrane is a sack around the abdominal organs. This membrane is semi-permeable allowing waste particles to go through it but preventing larger blood cells to penetrate the membrane. In this type of treatment, a patient has a plastic tube catheter surgically implanted into the abdominal wall. The patient's caregiver slowly empties the dialysate fluid into the catheter and exposes the blood to the dialysate through the peritoneal membrane. Similarly to the hemodialysis method, the waste particles are removed with the dialysate and are discarded.

The peritoneal dialysis method has distinct advantages as it allows to significantly reduce the time needed for the dialysate to clean the blood and remove the waste. Additionally, the patient can perform the procedure in a non-hospital setting or at thousands of locations around the world. Such type of treatment may be administered by a caregiver that may not be very experienced in other types of the dialysis procedure.

When the patient or a caregiver performs the dialysis treatment, the waste is drained into a bag or other container, which can then be emptied into a waste receptor, such as a sink or a toilet. Needless to say, the bag is quite heavy and cumbersome to handle. Various solutions have been offered to assist in disposing of the waste drained from a medical treatment device. For instance, U.S. Pat. No. 5,503,633 issued on Apr. 2, 1996 for "Ostomy Bag Cleaning Apparatus" discloses a device, which allows a patient to drain the waste from the ostomy bag into a toilet without disengaging the bag from the patient's body. The device uses a support for a patient at a sufficient height above a toilet bowl in the form of a platform with support bars that are mounted on the toilet. A hose attached to a house water supply allows cleaning of the ostomy bag while the patient is seated on the platform.

Another solution is offered in U.S. Patent Application No. 2002/0077608 published on Jun. 20, 2002 and entitled "Peritoneal Waste Bag Support and Drainage Device". The application discloses a collapsible table, which supports a peritoneal waste bag in a desired location, for instance, adjacent a toilet. A waste bag is placed on top of the table, with a plug of the waste bag being oriented above the toilet bowl. The height of the legs is adjusted to allow the table to be tilted and facilitate drainage of the waste bag content by gravity directly into the toilet.

Municipal and state plumbing codes allow drainage of dialysis waste directly into the municipal waste channels. However, the municipal and state codes also require that the drainage from a fixture, device or appliance that discharges directly into a sink or other waste receptor terminate at a point below the flood level end of the sink. The same codes also require that an unobstructed horizontal distance of be formed between the outside of the indirect waste pipe and the inside of the receiving sink or toilet so as to allow a backflow of sewerage to spill over the flood level rim of the receiving sink or receptacle and thereby prevent the backflow from reaching the fixture, device, or appliance which is served by the indirect waste pipe.

Another provision of the plumbing code requires that the check valve be installed in the drain or in the sewer or drainage system to prevent sewerage or drainage from backing into lower levels through the fixtures or devices not installed sufficiently above floor or drainage systems. Therefore, any device that drains into the sink or other receptacle must be provided with a check valve or have sufficient air gap in the drainage system as required by the code. The approved air gap is at least double the diameter of the supply pipe measured vertically above the overflow rim of the vessel and in ant case, less than 1 inch. While the devices suggested by the prior art may satisfy these requirements, there is a danger that the plumbing regulations may be difficult to follow when the waste bag is positioned atop of a tilted table, with the plug being positioned too close to the overflow level.

The present invention contemplates elimination of drawbacks associated with the prior art and provision of a mounting assembly for a drainage tube that can be mounted directly on the rim of a sink or other waste receptor with sufficient air gap to satisfy the plumbing regulations.

SUMMARY OF THE INVENTION

It is, therefore, an object of the present invention to provide a mounting assembly for a liquid waste line of a medical treatment apparatus that can be mounted on a rim of a sink or other waste receptor.

It is another object of the present invention to provide a mounting device that can be easily and efficiently engaged and disengaged from the rim of the waste receptor as required.

It is a further object of the present invention to provide a mounting device for a waste conduit that allows to satisfy the plumbing code requirements while being easy to use by a patient or a caregiver in a home or hospital environment.

These and other objects of the present invention are achieved through a provision of a mounting assembly that can be detachably secured to the nozzle of a discharge line for supporting the discharge nozzle above an opening of a waste receptor. The mounting assembly has a connector member, one end of which is securable to the discharge nozzle, and the other end of which carries a suction cup. The suction cup is mounted on a rim of the waste receptor, such as a sink or a toilet bowl. The connector member has sufficient longitudinal dimension to support the discharge nozzle at a pre-determined distance above the waste receptor. The connector member has a first portion having a longitudinal dimension of at least 0.5" (1.25 cm), a second portion unitary connected to the first portion at an angle of at least 90 degrees and a third portion, which hooks around the top of the suction cup. The easy-to-use and inexpensive mounting assembly of the present invention may be used by a caregiver in a home or hospital setting.

BRIEF DESCRIPTION OF THE DRAWINGS

Reference will now be made to the drawings, wherein like parts are designed by like numerals, and wherein.

DETAILED DESCRIPTION OF THE PREFERRED EMBODIMENT

Figure 1:
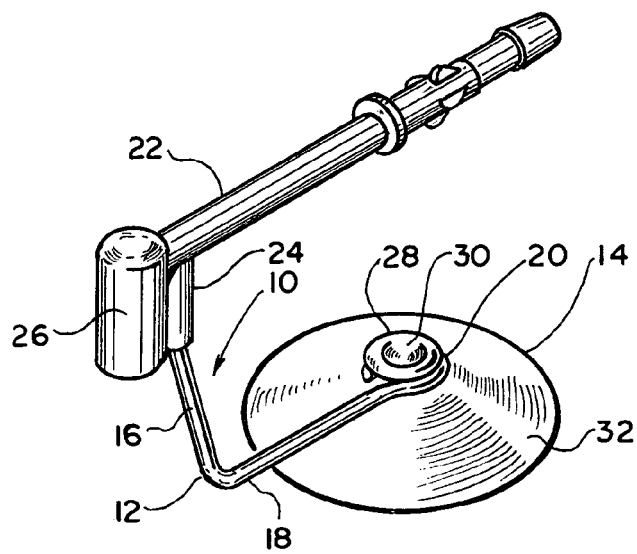
FIG. 1 is a perspective view of the mounting assembly in accordance with the present invention engaged with a nozzle of a drainage line.
Figure 2:
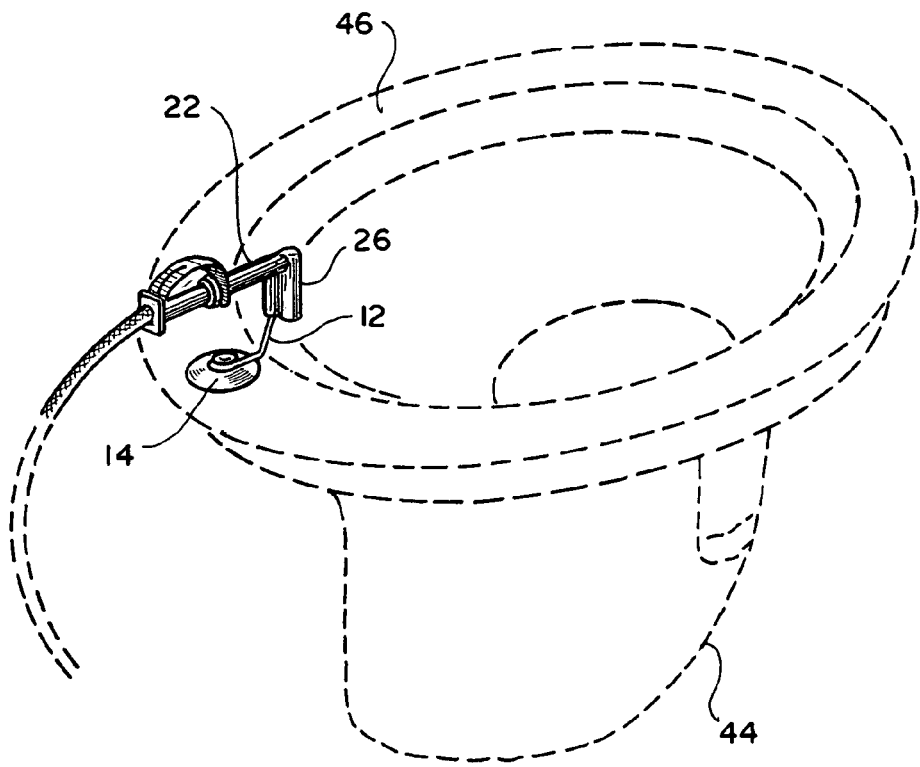
FIG. 2 is a perspective view illustrating the mounting assembly in use with a drainage conduit mounted on a rim of a toilet bowl.
Figure 3:
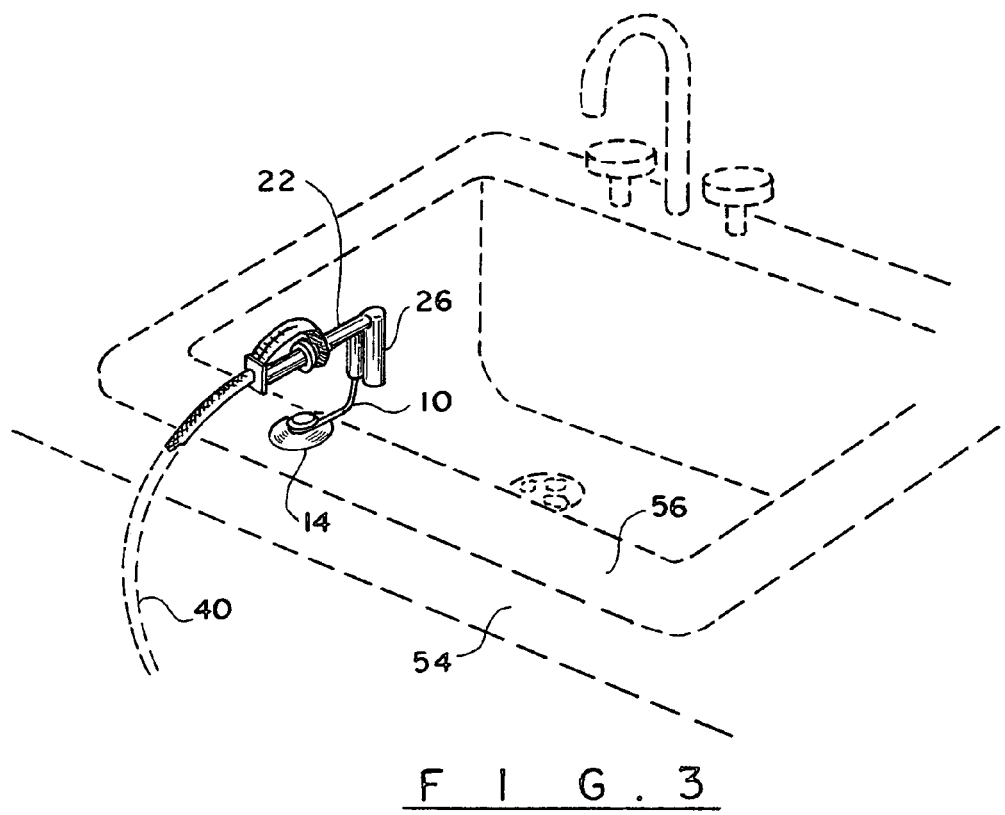
FIG. 3 is a perspective view of the mounting assembly of the present invention in use with a drainage conduit mounted on a rim of a sink.

Turning now to the drawings in more detail, numeral 10 designates the mounting assembly in accordance with the present invention. As can be seen in the drawings, the mounting assembly comprises a connector member 12 and a suction cup 14 detachably engageable with the connector 12. The connector member 12 is formed as a unitary body carrying the suction cup 14 on one end thereof and engageable with a discharge nozzle 22 of a waste conduit. The connector member 12 has a first portion 16, a second or middle portion 18, and a third portion 20. The first portion 16 of the connector member 12 is detachably engageable with a tube connector 24 of the nozzle 22.

It should be noted that the nozzle 22 and the tube connector 24 are of conventional design typically used with a discharge conduit 40 of a medical treatment apparatus 42, such as dialysis machine or other similar devices. The tube connector 24 is fixedly secured on the outside of the discharge part 26 of the nozzle 22. In conventional devices, the tube connector 24 serves as an engagement member for a connecting an attachment device. In the present invention, the first portion 16 is secured with the tube connector 24, thereby detachably securing the connector member 12 with the sleeve 24.

The second, middle portion 18 of the connector member 12 is unitary engaged with the first portion 16 and extends at 90 or greater degrees in relation to the longitudinal axis of the first portion 16. It is envisioned that the second, middle portion 18 may extend at an obtuse angle in relation to the longitudinal axis of the first portion 16 or at a right angle, depending on the particular requirements.

The third portion 20 of the connecting member 12 is bent to form a hook-shaped attachment member that partially encircles a top knob 28 of the suction cup 14. The second part 32 of the suction cup 14 is formed as a dome-shaped body, which carries the top knob 28 in the center thereof. The top knob 28 of the suction cup 14 has an upper surface 30 and a reduced diameter neck located below the upper surface 30. The third portion 20 of the connecting member 12 engages the reduced diameter neck, fitting between the top 28 and the dome-shaped body 32 of the suction cup 14.

The longitudinal dimension of the first portion 16 is selected to retain the discharge part 26 of the nozzle 22 at a sufficient distance above a rim of a waste receptor. In some of the embodiments, the longitudinal dimension of the first portion 16 is at least 0.5" (1.25 cm). In some of the embodiments, the first portion forms an obtuse angle with the second portion 18 so as to retain the discharge part 26 properly oriented above the waste receptor. In the preferred embodiment, the longitudinal dimension of the second portion 18 is at least as great as the radial dimension of the dome-shaped part 32 of the suction cup 14.

In operation, when drainage of a dialysate and other waste fluids is required, the user engages the mounting assembly 10 with the outlet nozzle 22. The portion 16 is attached to the tube connector 24, thereby temporarily securing the mounting assembly 10 on the nozzle 22. The waste discharge line 40 extends from the medical treatment apparatus 42 to a desired location, for instance, adjacent a toilet bowl 44. A rim 46 of the toilet bowl 44 serves as a mounting surface for the assembly 10. A patient 50 may be located some distance from the waste receptor 44.

Figure 4:
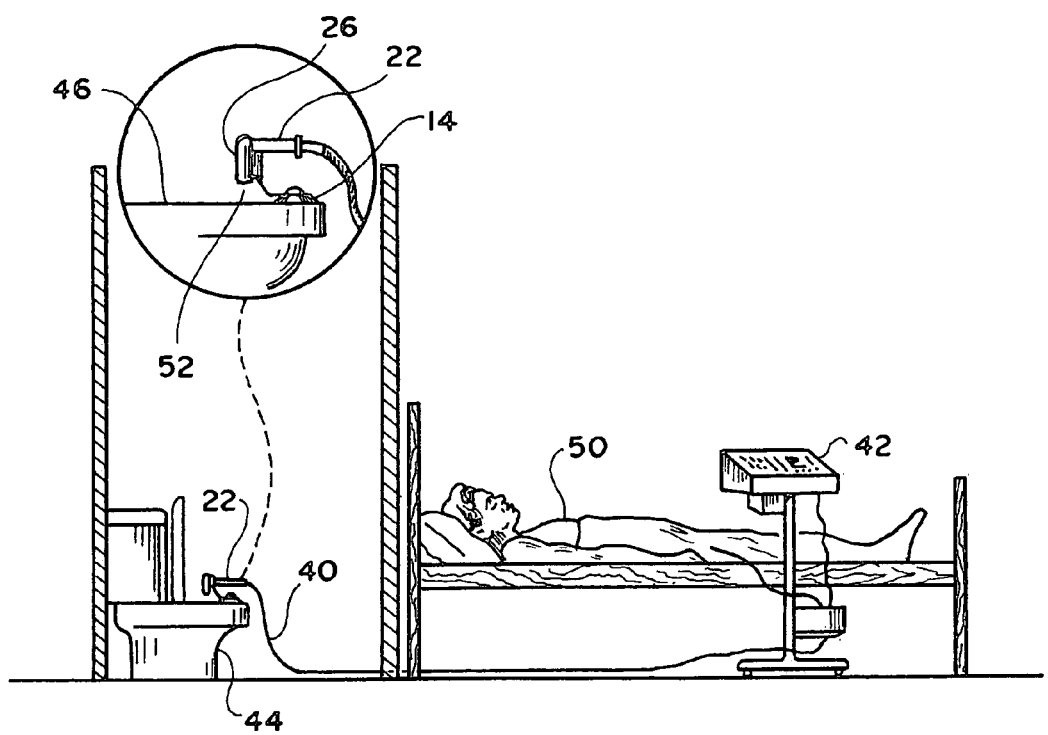
FIG. 4 is a schematic view illustrating position of the mounting assembly on a rim of a toilet bowl and connected to a drainage conduit of a medical treatment apparatus.

The waste material with dialysate circulated from the blood stream by the dialysis machine 42 is conducted through the waste conduit 40 into the nozzle 22. The discharge tube 26 of the nozzle 22 is extended above the toilet bowl 44 so that a sufficient air gap 52 (FIG. 4) is formed between the opening in the tube 26 and the surface of water (not shown) in the toilet bowl 44. The caregiver then attaches the suction cup 14 to firmly engage the suction cup 14 with the rim 46. The connector member 12 retains the opening of the discharge tube 26 above the rim 46. The waste fluid is then allowed to discharge through the nozzle 22 and the tube 26 directly into the toilet bowl 44 and into the municipal sewerage lines.

The mounting assembly 10 can be used for positioning the outlet nozzle 22 of the conduit 40 above a standard sink 54. In this case, the suction cup 14 is engaged with the rim 56 of the sink 54. The outlet opening of the discharge tube 26 is oriented above the waste receptor, or sink 54. The waste from the dialysis machine is allowed to travel through the discharge conduit 40, nozzle 22 and out of the tube 26 to be discharged directly into the sink 54.

The connecting member 12 of the mounting assembly 10 is formed as a thin rod made of a non-corrosive material. The suction cup 14 is formed from a resilient, flexible plastic allowing the suction cup 14 to form the vacuum under the dome and secure the mounting assembly 10 on the sink or other receptacle.

Many changes and modifications can be made in the design of the present invention without departing from the spirit thereof. I, therefore, pray that my rights to the present invention be limited only by the scope of the appended claims.

I claim:

1. A method of supporting a liquid waste discharge line for evacuating waste from a medical treatment apparatus, said liquid waste discharge line comprising a discharge nozzle with a discharge opening and a tubular connector carried by the discharge nozzle, said method comprising the steps of:

providing a connector member and a suction cup attached to the connector member;

securing one end of the connector member to the tubular connector of the discharge nozzle such that the one end of the connector member frictionally firmly engages within the tubular connector; and mounting the suction cup on a rim of a waste receptor such that the discharge opening extends a distance above the waste receptor, thereby supporting the discharge nozzle on the waste receptor and facilitating evacuation of liquid waste from the medical treatment apparatus directly into the waste receptor.

2. The method of claim 1, further comprising the steps of providing the connector member with a first portion configured to frictionally engage within the tubular connector, a second portion extending at an angle to the first portion and a third portion attachable to a top of the suction cup.

3. The method of claim 2, further comprising the step of providing the first portion of a longitudinal dimension sufficient to elevate the discharge opening of the discharge nozzle to a pre-determined distance above a rim of the waste receptor.

4. The method of claim 2, further comprising the step of forming the second portion of the connector member of sufficient dimensions at least equal to radial dimension of the suction cup.

5. The method of claim 1, further comprising the step of providing said suction cup with an enlarged top knob, a dome-shaped cup part and a reduced diameter neck connecting the knob to the cup part, and wherein said hook-shaped attachment member wraps about at least a part of the circumference of the neck portion such that the top knob prevents disengagement of the hook-shaped attachment member from the neck.

* * * * *